United States Patent [19]

Morii et al.

[11] Patent Number: 5,158,882

[45] Date of Patent: Oct. 27, 1992

[54] METHOD FOR PURIFYING A CRUDE TISSUE PLASMINOGEN ACTIVATOR PREPARATION

[75] Inventors: Mitsuyoshi Morii, Yokohama; Nobuhiro Kawashima, Sagamihara; Kunizo Mori; Masaharu Ohoka, both of Yokohama, all of Japan

[73] Assignee: Mitsui Toatsu Chemical Incorporated, Tokyo, Japan

[21] Appl. No.: 842,759

[22] Filed: Feb. 28, 1992

Related U.S. Application Data

[63] Continuation of Ser. No. 399,882, Aug. 29, 1989, abandoned.

[30] Foreign Application Priority Data

Sep. 5, 1988 [JP] Japan .................................. 63-221843

[51] Int. Cl.⁵ .......................... C12N 9/64; C12N 9/48
[52] U.S. Cl. .................................... 435/226; 435/212; 435/815
[58] Field of Search ...................... 435/226, 212, 815

[56] References Cited

U.S. PATENT DOCUMENTS

| | | | |
|---|---|---|---|
| 4,104,125 | 8/1978 | Takechi et al. | 435/815 |
| 4,264,738 | 4/1981 | Stepanov et al. | 435/219 |
| 4,374,926 | 2/1983 | Stern | 435/219 |

FOREIGN PATENT DOCUMENTS 0261941 3/1988 European Pat. Off. ............ 435/212

OTHER PUBLICATIONS

Scopes, "Protein Purification Principles and Practice", 2nd edition, 1987, pp. 110, 111, 122, 123.

Primary Examiner—Douglas W. Robinson
Assistant Examiner—Michael V. Meller
Attorney, Agent, or Firm—Nixon & Vanderhye

[57] ABSTRACT

Separation of tPA and undesired proteins is securely and effectivity accomplished by using a cation-exchanger in the two step procedure for selective elution of undesired proteins from the cation-exchanger on which tPA and undesired proteins are adsorbed: undesired proteins having the pI equivalent to or lower than that of tPA was eluted out in the first step and then undesired proteins having the pI equivalent to or higher than were eluted in the second step.

2 Claims, No Drawings

METHOD FOR PURIFYING A CRUDE TISSUE PLASMINOGEN ACTIVATOR PREPARATION

This is a continuation of application Ser. No. 07/339,882, filed Aug. 29, 1989, now abandoned.

BACKGROUND OF THE INVENTION

1. Field of the Invention

This invention relates to a method for purifying human tissue plasminogen activator (hereinafter referred to as tPA). More specifically, this invention relates to a method for isolating and purifying tPA having a molecular weight of about 70,000 daltons by bringing a crude tPA preparation containing tPA and other undesired proteins into contact with a cation-exchange resin.

2. Description of the Prior Art tPA is a protein which has a molecular weight of about 70,000 daltons and is produced in a tissue of a higher animal, serves to activate plasminogen, a precursor of plasmin which is a proteolytic enzyme specific to fibrin.

In order to produce tPA for the pharmaceutical use, it is necessary to sufficiently remove undesired heteroantigenic proteins. If tPA is contaminated with such undesired proteins, these proteins exert the antigenicity in the human body to causes side effects such as anaphylactic shock when administered.

Types of undesired heteroantigenic proteins incorporated as contaminants in the manufacturing processes vary depending on method of cultivation of cells and purification procedure used. In the manufacturing procedure which includes a process of cultivating cells capable of producing tPA, a large amount of undesired heteroantigenic proteins are contained in resultant culture fluids, as constituents of a medium solution and as excretions by the cells.

Representative methods for cultivation include that with the use of a medium containing fetal calf serum and that with the use of a serum-free medium.

In the case where fetal calf serum is used for cultivation, the fetal calf serum contains a group of undesired heteroantigenic proteins which exert antigenicity to human. Proteins derived from fetal calf serum vary but most of them have the pI (isoelectric point) in the range between 4 and 6.

Furthermore, in the case where a serum-free medium is used, substances required for cultivation must be added to the medium depending on the cells used.

Among the substances required for cultivation, as to proteins, hormones, such as insulin, and transferrin are frequently used. The pI values of insulin and transferrin are approximately in the range between 5 and 6.

tPA is known to have two molecular forms, single-chain tPA and double-chain tPA. It is known that, particularly in a method for preparing single-chain tPA, protease inhibitors such as aprotinin are added to a medium during cultivation of cells for the production of tPA.

The protease inhibitors used are also undesired heteroantigenic proteins. The pI of aprotinin is in the range 10–10.5.

Furthermore, tPA containing fluids obtained by partially purifying the above culture fluids by the manner described below can also include undesired proteins.

For the purification of tPA, various types of affinity chromatography have been used. Known examples include concanavalin A-Sepharose (Rijken, D. C. and Collen, D. (1981) J. Biol. Chem. 256, 7035–7041), erythrina trypsin inhibitor (ETI)-Sepharose (Heussen, C., et al. (1984) J. Biol. Chem. 259, 11635–11638), anti-tPA and antibody-Sepharose (Ranby M., et al. (1982) FEBS Lett 146, 289–292) and fibrin-Sepharose (U.S. Pat. No. 4,505,893). Outflow of these immobilized proteins, though in a small amount, is observed during operation. Also, these proteins are undesired heteroantigenic proteins. The ranges of the pI of these proteins are 4.4 to 5.5 for concanavalin, 4.5 to 5.5 for ETI, 5.8 to 7.3 for immunoglobulin G and 5.5 to 5.8 for fibrinogen.

In view of methods for preparing tPA, the present inventors had been intensively investigated means for removing these potential heteroantigenic proteins. As a result, the inventors found that a method with the use of cation-exchange resins is particularly advantageous, and thus completed the present invention.

The use of a cation-exchanger for purification of tPA is known (Japanese Patent Laid-Open No. 174727/1985), in which, however, the cation-exchanger is used for recovering tPA fractions for the purpose of partial purification, which is different from the use of the cation-exchanger in the present invention.

SUMMARY OF THE INVENTION

In the course of intensive investigations on methods for purifying tPA using cation-exchangers, the present inventors found that reliable and effective separation of tPA from other undesired proteins can be accomplished by dividing a eluting process for selective elution of undesired proteins from the cation exchanger on which tPA and other undesired proteins are adsorbed into two steps and by carrying out the steps in a defined order: one step to elute undesired proteins having the pI values equivalent to or lower than that of tPA, and the other step to elute undesired proteins having the pI values equivalent to or higher than that of tPA. Also, the present inventors found the appropriate range of the pH for eluents to be used in the two steps, and thus completed the present invention.

An object of the present invention is to provide a method for purifying tPA, from a crude tPA preparation obtained, for example, by cultivating tPA-producing cells, by using cation-exchange resins which can securely and effectively remove undesired proteins including those which may cause side effects when used as pharmaceuticals.

According to the method of present invention, tPA can be securely and effectively separated from undesired substances, in particular proteins, which may cause side effects, such as pyrogen, and other undesired proteins. Moreover, tPA which is thus separated from undesired proteins can be used as pharmaceuticals as it is without being subjected to concentration or desalting step, since it is eluted in a concentrated form from a cation exchange resins. Furthermore, tPA is obtained in high yield.

DETAILED DESCRIPTION OF THE PREFERRED EMBODIMENTS

A method according to the present invention for purifying tPA comprises the steps of:

(a) contacting a crude tPA preparation containing tPA and undesired proteins with a cation-exchanger to allow said tPA and undesired proteins to adsorb to said cation-exchanger;

(b) treating said cation-exchanger with an eluent having a pH in the range between 5.2 to 6.5 to elute undesired proteins having the pI values equivalent to or lower than that of said tPA;

(c) treating said cation-exchanger followed by the step (b) with an eluent having a pH in the range between 2.8 to 3.5 and then eluting undesired proteins having the pI values equivalent to or higher than that of said tPA; and (d) eluting said tPA from the cation-exchanger followed by the steps (b) and (c).

Examples of the crude tPA preparations to be brought into contact with the cation-exchanger in the step (a) include partially purified fractions obtained by the various purification methods described above from culture supernatants obtained by cultivating tPA-producing cells (including recombinant cells); extracts from cultured cells; and extracts from tissues of higher animals. All these crude preparation contain or are suspected to contain various undesired proteins other than tPA as described above.

tPA to be purified according to the present invention has a molecular weight of about 70,000 daltons and the pI in the range 6 to 8.

Examples of cation-exchangers to be used in the step (a) include those comprising a carboxymethyl groups as cation-exchange groups and polysaccharides or acrylamides as water-insoluble carriers.

Application of the crude preparation onto the cation-exchanger in the step (a) can be carried out under the conditions where tPA contained in the crude preparation be adsorbed to the cation-exchanger. For example, the adsorption to the cation-exchanger can be carried out by passing the crude tPA solution which is weakly acid, preferably has a pH in the range of 4.5 to 5.0, through the cation-exchanger.

The step (b) can be carried out by washing the cation-exchanger with an eluent at a pH in the range so that undesired proteins having the pI values equivalent to or lower than that of tPA are removed. Said pH range to be used is in the range between 5.2 to 6.5.

In the step (b), other conditions including temperature and salt concentration for elution are appropriately selected so that a large amount of tPA adsorbed to the cation-exchanger is not eluted.

The step (c) can be carried out by washing out undesired proteins having the pI values equivalent to or higher than that of tPA with an eluent having a pH lower than the pKa value of the cation-exchange. A solution having a pH in the range between 2.8 and 3.5 is used for said eluent.

In the step (c), other conditions including temperature and salt concentration for elution are appropriately selected so that tPA adsorbed to the cation-exchanger is not eluted in a large amount.

The step (d) can be carried out by passing through the cation-exchanger a solution, having a pH at which tPA is stable, which can effectively elute tPA adsorbed to the cation-exchanger.

An example of the solution to be used is that having a pH in the range 2 to 10 and a necessary salt concentration; inter alia, a solution having a pH in the range 2 to 3 can be preferably used to elute and obtain concentrated tPA under the condition of a low salt concentration.

Since salt concentrations required for elution of tPA are different depending on the types of carriers of cation-exchangers used, they are selected to be appropriate to individual cation-exchangers.

For example, when NaCl is used, the following minimum salt concentrations are required in eluents having different pH ranges as follows:

| pH of eluent | Minimum salt concentration required (M) |
| --- | --- |
| 2–2.5 | 0 |
| 2.5–3.2 | approx. 0.05 |
| 3.2–6.0 | approx. 0.1 |
| 6.0–8.5 | approx. 0.05 |
| 8.5–10.0 | approx. 0.01 |

For example, in the case where CM-trisacryl M (IBF Biotechics, France) is used, appropriate salt concentrations equivalent to or higher than the minimum salt concentrations given above can be used; in the case where CM-Sepharose is used, about 1.5 to 3 times the minimum salt concentrations given above are used.

The maximum salt concentration in an eluent may be the saturation point of the salt.

In the purification methods according to the present invention, for example, the following characteristic features are confirmed.

Although proteins having the pI higher than that of tPA is expected to be eluted after tPA when proteins adsorbed on the cation-exchanger subject to be eluted in order of descending pH, the order of the elution is reversed; for example, aprotinin which pI is in the range 10 to 10.5 is eluted before tPA.

This result confirms that tPA must be one of the strongest adsorbed protein to the cation-exchanger among proteins. This should be due to not only ionic environment but the affinity of tPA to the resin (water-insoluble carrier). This fact is noticed to use more extreme condition such as lower pH that the pK of carboxymethyl group for removal of undesired proteins.

Furthermore, although proteins having the pI lower than that of tPA is expected to be separated from tPA in the step (b), ETI and anti-tPA antibody, for example, if adsorbed to the cation-exchanger, can not be separated from tPA, because they bind to tPA at the pH around the neutral range. However, at the pH in the range used in the step (c) after the step (b), the ETI and anti-tPA antibody tPA are dissociated from tPA and thus can be eluted out so as to easily separated from tPA.

Preferred embodiments of the present invention are as follows.

EXAMPLE 1

Bowes melanoma cells (ATCC CRL 1424 G361) were cultured in a RPMI-1640 tissue culture medium supplemented with 10% heat-inactivated (at 56° C. for 30 minutes) fetal calf serum and then the resultant culture was washed once. Cultivation was continued for another 24 hours in the same medium, without serum, supplemented with 40 KIU (kallikrein inhibitor units)/ml of aprotinin. The culture supernatant was collected and used as a recovered fluid.

A sample used for application to cation-exchange resins is prepared as follows:

To the recovered fluid was added NaCl to give a final concentration of 1M and the resultant fluid was applied on an anti-human tPA antibody-Sepharose column (10 mg antibody/ml resins) which had been equilibrated with 50 mM phosphate buffer containing 1M NaCl (pH 7.5). The column was washed with an equilibration buffer solution and then a tPA fraction was eluted with a glycine-HCl buffer solution containing 2M ammonium thiocyanate (pH 3.5). The activity of tPA in the elute was 88% of the activity applied on the column. Ammonium sulfate was dissolved in the eluate at a concentration of 300 g/l and the solution was stirred at 4° C. overnight and then centrifuged to recover precipitate. The precipitate was dissolved in a 0.05M sodium dihydrogenphosphate solution (pH 4.5) and subjected to dialysis against the same buffer solution. The resultant dialyzed solution was used as a sample. This sample contained undesired proteins derived from the culture and anti-human tPA antibody as well as tPA. The amount of undesired proteins derived from the culture fluid was determined, using fetal calf serum-derived proteins and aprotinin as indices, by enzyme immunoassay (EIA) with antibodies against these proteins. Proteins derived from fetal calf serum and aprotinin were 45 μg and 70 ng, respectively. Anti-human tPA antibody was 450 μg.

The sample was passed through a CM-trisacryl M column (IBF) (5 ml) which had been equilibrated with 0.05M sodium dihydrogenphosphate solution (pH 4.5). The passed through fraction was collected and subjected to the determination of plasminogen-dependent fibrinolytic activity. Activity was not detected at all.

Subsequently, the column was washed first with 100 ml of a 0.05M phosphate buffer solution (pH 5.8) to remove undesired proteins having the pI values equivalent to or lower than that of tPA, and then with 100 ml of a 0.05M glycine-HCl buffer solution (pH 3.2) to remove undesired proteins having the pI values equivalent to or higher than that of tPA. tPA activity in the eluates was about 5% of the activity applied on the column. Finally, tPA was eluted with 50 ml of a 0.1M sodium dihydrogenphosphate-phosphoric acid buffer solution (pH 2.5). The tPA activity in the eluate was about 90% of the activity applied on the column.

The eluted fraction was subjected to SDS-polyacrylamide gel electrophoresis and then to staining, which revealed a single band corresponding to a molecular weight of about 70,000 daltons. The amounts of undesired proteins per mg of tPA were about 20 ng for those derived from fetal calf serum, about 5 ng for aprotinin and about 20 ng for anti-human tPA antibody.

EXAMPLE 2

A sample to be applied to cation-exchange resins was prepared by the following procedure:

Two liters of a culture supernatant obtained by cultivating mouse fibroblast cells (mouse C127I ATCC CRL 1616) transformed with human tPA gene in a RPMI-1640 tissue culture medium containing insulin, transferrin and 40 KIU/ml of aprotinin was applied onto 20 ml of a fibrin-Sepharose column (20 mg fibrin/ml resins) equilibrated with a 0.05M phosphate buffer solution containing 0.15M NaCl (pH 7.5). The column with proteins adsorbed was washed with 400 ml of a 0.05M phosphate buffer solution containing 1M NaCl (pH 7.5).

Subsequently, proteins were eluted with 200 ml of a 0.05M disodium hydrogenphosphate-NaOH solution containing 0.5M lysine (pH 10.0). The plasminogen-dependent fibrin activity of the eluate was determined, which revealed that about 90% of the activity applied on the column was recovered. The elute fraction was dialyzed against a 50 ml sodium dihydrogenphosphate solution (pH 4.5) and the resultant solution as a sample was applied onto 20 ml of a CM-trisacryl M column equilibrated with a 50 mM sodium dihydrogenphosphate solution (pH 4.5). The resins with adsorbed proteins were washed first with 400 ml of a 25 mM phosphate buffer solution (pH 6.0) to remove undesired proteins having the pI equivalent to or lower than that of tPA, and then with 400 ml of a 0.05M glycine-HCl buffer solution (pH 3.2) to remove undesired proteins having the pI equivalent to or higher than that of tPA. Finally, tPA was eluted with 100 ml of a 50 mM sodium dihydrogenphosphate-phosphoric acid buffer solution containing 50 mM NaCl (pH 2.5).

The recovery of tPA was about 90% and staining after SDS polyacrylamide gel electrophoresis of the tPA fraction revealed a single band with a molecular weight of about 70,000 daltons. Remaining antigenic substances were determined by enzyme immunoassay using anti-insulin antibody, anti-transferrin antibody, anti-fibrinogen antibody and anti-aprotinin antibody, which revealed that amounts of remaining proteins per mg of tPA were less than 5 ng for insulin, less than 10 ng transferrin, about 30 ng for fibrinogen and about 2 ng for aprotinin.

EXAMPLE 3

Ten litters of a culture supernatant obtained by cultivating human fetal pulmonary cells (ATCC MRC 5 CCL171) in a RPMI-1640 tissue culture medium containing 10% heat-inactivated (at 56° C. for 30 minutes) fetal calf serum and 20 KIU/ml of aprotinin was applied onto 10 ml of an ETI-Sepharose column on which erythrina trypsin inhibitor (ETI) had been immobilized (5 mg ETI/ml resins). After washing the column with 200 ml of a 0.05M phosphate buffer solution containing 2M NaCl (pH 7.5), proteins were eluted with 50 ml of a citric acid buffer solution containing 0.05M NaCl (pH 4.7). Recovery of the activity in the eluted fraction was about 40% of the activity applied on the column. The eluate was applied as a sample onto 10 ml of CM-Sepharose column equilibrated with a 0.05M citric acid buffer solution containing 50 mM NaCl (pH 4.7). The column with proteins adsorbed was washed first with 200 ml of a 0.05M phosphate buffer solution containing 50 mM NaCl (pH 6.0) to remove undesired proteins having the pI equivalent to or lower than that of tPA, and then with 200 ml of a 0.05M citric acid buffer solution containing 50 mM NaCl (pH 2.8) to remove undesired proteins having the pI equivalent to or higher than that of tPA. Subsequently, tPA was eluted with 50 ml of a 0.05M sodium dihydrogenphosphate-phosphoric acid buffer solution containing 50 mM NaCl (pH 2.0).

Recovery of tPA activity was about 90% of the activity applied on the column. Staining after SDS-polyacrylamide gel electrophoresis confirmed a single band corresponding to a molecular weight of about 70,000 daltons.

Remaining antigenic substances are examined by enzyme immunoassay using anti-fetal calf serum antibody, anti-ETI antibody and anti-aprotinin antibody, which revealed that the proteins remaining per mg tPA were about 30 ng for fetal calf serum, about about 5 ng for ETI and less than 1 ng for aprotinin.

What is claimed is:

1. A method for purifying a crude tPA preparation, containing tPA and undesired proteins, said method comprising the successive steps of:

(a) contacting said crude preparation with a cation-exchanger having a carboxymethyl group as the cation-exchange group to adsorb the APA and proteins onto said cation-exchanger;
(b) washing said cation-exchanger with an eluent having a pH in the range between 5.2 and 6.5 at a salt concentration at which the tPA is not eluted to elute the undesired proteins having PI values equivalent to or lower than that of said tPA;
(c) washing said cation-exchanger with an eluent having a pH in the range between 2.8 and 3.5 at a salt concentration at which the tPA is not eluted to elute the undesired proteins having the PI values equivalent to or higher than that of said tPA: and
(d) eluting tPA having a molecular weight of about 70,000 daltons and a PI value in the range 6 to 8 from the cation-exchanger at a pH of below 2.8.

2. The method of claim 1, wherein the crude tPA preparation has a pH in the range 4.5 to 5.0

* * * * *